United States Patent

Przybilla et al.

[11] Patent Number: 5,958,251
[45] Date of Patent: Sep. 28, 1999

[54] METHOD OF AND APPARATUS FOR THE PURIFICATION OF GASES AND LIQUIDS

[75] Inventors: Karl Przybilla, Vaduz; Gerold Paesold, Triesen, both of Liechtenstein

[73] Assignee: Ultralight AG, Schaanwald, Liechtenstein

[21] Appl. No.: 08/793,392

[22] PCT Filed: Aug. 24, 1995

[86] PCT No.: PCT/IB95/00682

§ 371 Date: Feb. 24, 1997

§ 102(e) Date: Feb. 24, 1997

[87] PCT Pub. No.: WO96/06045

PCT Pub. Date: Feb. 29, 1996

[30] Foreign Application Priority Data

Aug. 25, 1994 [DE] Germany ............... P 44 30 231

[51] Int. Cl.$^6$ .................................................. C02F 1/30
[52] U.S. Cl. ................. 210/748; 96/272; 210/150; 261/112.1; 422/23; 422/24
[58] Field of Search ................... 210/748, 150; 96/272; 261/112.1; 422/22, 23, 24, 121

[56] References Cited

U.S. PATENT DOCUMENTS

| | | | |
|---|---|---|---|
| 4,028,246 | 6/1977 | Lund et al. | 210/151 |
| 4,530,822 | 7/1985 | Ashley et al. | 423/242 |
| 4,755,292 | 7/1988 | Merriam | 210/192 |
| 4,940,519 | 7/1990 | Dames . | |
| 4,980,098 | 12/1990 | Connery | 261/112.1 |
| 5,372,781 | 12/1994 | Hallett et al. | 422/24 |

FOREIGN PATENT DOCUMENTS

| | | |
|---|---|---|
| 0 146 885 B1 | 7/1985 | European Pat. Off. . |
| 25 27 009 | 12/1976 | Germany . |
| 35 25 975 A1 | 1/1987 | Germany . |
| 38 37 905 A1 | 5/1990 | Germany . |
| 39 03 549 A1 | 8/1990 | Germany . |
| 40 30 021 A1 | 4/1991 | Germany . |
| 40 05 488 A1 | 8/1991 | Germany . |
| 90 17 684 | 1/1992 | Germany . |
| 41 36 949 A1 | 5/1993 | Germany . |
| 41 37 301 C1 | 6/1993 | Germany . |
| 42 10 509 A1 | 10/1993 | Germany . |
| 42 24 130 A1 | 3/1994 | Germany . |
| 43 04 444 A1 | 8/1994 | Germany . |
| 43 07 204 A1 | 9/1994 | Germany . |
| WO 86/02859 | 5/1986 | WIPO . |

OTHER PUBLICATIONS

CAV, Jan. 1994, article entitled "UV–katalysierte Nassoxidation" ("UV–catalyzed wet oxidation").

*Primary Examiner*—Jay H. Woo
*Assistant Examiner*—Betsey J. Morrison
*Attorney, Agent, or Firm*—Frishauf, Holtz, Goodman, Langer & Chick, P.C.

[57] ABSTRACT

In a method of purifying contaminated liquids and gases, a continuous surface film (31) is produced by means of a nozzle (15) and is simultaneously irradiated by a suitable radiation source (17), e.g. an UV lamp. The surface film (31) is discharged as a falling or trickling film (33) which is also exposed to the radiation. A gas for purification is passed through the surface film (31). In these conditions the pollution particles and other pollutants in the gas are absorbed by the liquid. The advantage of the process described is that decomposition of the pollutants can take place both in the gas phase and in the liquid phase. Gas pollutants which are not decomposed in the gas phase are absorbed by the liquid, where they are finally decomposed. With the present invention liquids and gases can be treated simultaneously.

28 Claims, 4 Drawing Sheets

METHOD OF AND APPARATUS FOR THE PURIFICATION OF GASES AND LIQUIDS

BACKGROUND OF THE INVENTION

Field of the Invention

This invention relates to a method and apparatus for the treatment of polluted gases and liquids.

In order to be able effectively to irradiate with UV light in a continuously operating throughflow reactor highly contaminated waste water having a low light transmission, DE-A-40 05 488 proposes the use of a falling film or flowing film reactor. The falling film reactor consists of a reactor tube in which an UV radiator surrounded by a quartz protective tube is arranged concentrically. The reactor tube has an inlet for the liquid for treatment at the top and an outlet at the bottom. A restrictor at the top end of the reactor tube ensures that the water for treatment flows at a slightly positive pressure through the reactor tube, which is open at the bottom. The water flows in the form of a falling film down the inner walls of the reactor tube. There is no contact between the water and the quartz protective tube. Mass transfer with the surrounding gas takes place at the surface of the film. DE40 05 488 proposes utilising this effect to strip readily volatile substances. A disadvantage of the described reactor is that it is suitable only for the detoxification of drinking water of liquids. The reactor is not considered for use for air purification since the contact times of the air with the falling film would be too short and the mass transfer taking place under these conditions would be inadequate in the light of experience. Accordingly the only consideration has been to utilise the mass transfer from the liquid phase to the gas phase to strip readily volatile substances out of the liquid phase. DE-A-38 37 905 proposes an apparatus for the treatment of liquids and/or gases by means of UV light sources wherein the UV lamps of different emission spectra are used simultaneously. The UV lamps are disposed in or around a tubular reaction chamber. The medium for treatment is passed through the reaction chamber in concurrent or countercurrent flow, depending upon the reaction chamber construction. Although this apparatus may be suitable for the treatment of liquids, its utility for the effective treatment of gases appears doubtful. Many organic compounds, e.g. benzene, toluene, etc., occurring in polluted waste air are admittedly UV-light-absorbent but they are chemically extremely stable so that the most that can partially occur is a breaking up of the molecules during their passage through the reactor. Known methods of treating polluted gases very often therefore make use of a wet stage in order to remove adhering pollutants from the gas. In the wet stage the gas is contacted with a liquid, e.g. in a Raschig column or by means of a spray mist in order to convert the pollutants to the liquid phase. This operation can then be followed by further treatments.

SUMMARY OF THE INVENTION

The object of the present invention is to provide a method which is suitable equally for the purification of gases and/or liquids and which substantially overcomes the disadvantages referred to above. The invention is also to provide a reactor for performing the process.

According to the invention, this is achieved by a method of the kind referred to in the introduction, wherein a cohesive surface film is formed in the reactor by means of a nozzle and the gas is passed through the surface film so that a mass transfer can take place from the gas phase to the liquid phase. The liquid film produced by the nozzle is in the form of a closed surface film or impact film through which the gas for purification is pressed without destroying this cohesive film. The passage of the gas can take place mainly at the edge zone of the surface film. In these conditions, the surface film acts as a narrow-pore filter which allows a practically complete contacting of gas and liquid.

This method has the advantage that the pollutants not decomposed in the gas phase by the irradiation can be practically completely transferred to liquid by contact therewith. In contrast to DE-A-40 05 488, the method according to the invention is suitable for the treatment of liquids and/or gases. In many cases, the pollutants occur in fact in both waste air and in waste water.

Advantageously, the gas and the liquid are irradiated simultaneously. As a result of the simultaneous irradiation of the liquid and the gas, the pollutants not decomposed in the gas phase can be destroyed in the liquid phase. As a rule, the pollutants for removal have a different reactivity in the gas and liquid phases so that the purification effect can be substantially improved by the irradiation of gas and (washing) liquid. In addition, due to the decomposition taking place in the liquid phase, a low solubility of the pollutants in the liquid is already sufficient to enable them to be extensively removed from the gas flow. Since the pollutants are continuously destroyed, the liquid can repeatedly absorb new pollutants. The absorption capacity or saturation of the liquid is therefore practically never reached.

In contrast to conventional methods in which contacting between the gas and liquid takes place by means of a spray nozzle and a Raschig column and radiation exposure is practically impossible, in the method according to the invention the pollutants are subjected to the radiation without impairment so that optimal irradiation is guaranteed.

The gas is advantageously supplied in countercurrent flow to the falling film. Consequently the gas can already come into contact with the falling film before passing through the surface film. A rotating surface film is advantageously produced in the reactor. A rotating surface film is particularly advantageous because the gas flow is already brought into rotation before contact with the surface film so that particles are conveyed outwardly and in these conditions the gas can repeatedly come into contact with the liquid. A method and a nozzle for producing a rotating radially flowing surface film is described in EP-A-0 204 709, the contents of which are hereby incorporated in this application. In contrast to the method of EP-A-0 204 709, the pollutants in the present method are thus not only removed from the gas flow but decomposed to a large extent—either already in the gas phase or, at the latest, in the liquid—so that there is no need for disposal of the washing liquid or any subsequent treatment. The falling, flowing or trickling film has the advantage that even turbid liquids having low transmission for the radiation used can be intensively irradiated and decomposed not only on the impact—or surface screen (film) but during the entire flowing time. The pollutants in the liquid may be present in a relatively high concentration.

Advantageously, there is admixed with the gas and/or liquid a reagent or a compound e.g. oxygen, which is activatable by irradiation and which can react with at least some of the pollutants in the gas phase. The efficiency of the method can thus be further increased. Ozone can be formed in situ from oxygen by irradiation in the gas flow, which is often polluted air, without the need to use ozone generators. The ozone formed can already react with unsaturated organic compounds in the gas phase. A further advantage is that the ozone formed can be removed from the gas flow by the surface film. In addition, ozone constitutes a strong oxidant in water. It is advantageous to add to the liquid a compound activatable by irradiation. A compound of this kind, for example is hydrogen peroxide, which by UV irradiation forms the extremely reactive hydroxyl radicals. These radicals attack most organic molecules. Catalysts, such as iron or manganese salts, etc., can be added to the liquid in order to boost the decomposition of the organic pollutants.

Advantageously, the liquid is circulated. Consequently a small quantity of liquid is sufficient for performing the process. Polluted liquid or reagents can be added continuously or at intervals to the liquid circulating in the reactor. It is also possible to treat polluted gas and polluted liquid simultaneously. This may be of advantage in many industries, e.g. the paint industry, since very often it is not only the waste air, but also the waste water can be purified by the same process simultaneously. Advantageously, the gas flow can be partially circulated. This can be provided in those cases in which the solubility of the pollutants in the gas is low in the liquid phase or the transfer of the gaseous pollutants to the liquid phase is incomplete for some other reasons on passage through the surface film. Another advantage is obtained if the concentration of the pollutants in the liquid is measured and on this basis the supply and discharge of polluted gas and/or polluted liquid and/or the number of passes of the liquid and/or the gas and/or the intensity of the radiation are controlled and, where applicable, regulated. This allows fully automatic control of the purification process. The supply and discharge of liquid or the number of passes of the liquid can be regulated by selective measurement, for example, of the radiation absorption or radiation emission of the liquid and of the gases at more than one point, preferably at three points, namely the inlet, the outlet and therebetween, and in many cases it is not necessary to use more than one reactor. Alternatively or additionally the intensity of the radiation source can also be adjusted by this regulation. Selective radiators are recommended for optimisation of the process, i.e. radiators having an emission spectrum which is optimized in respect of the pollutants for removal. In the same way, other characteristics, such as the pH, the redox potential, the conductivity, the temperature etc. can be measured and their signals used for regulating the process.

The invention also relates to an apparatus for performing the method, which is characterised in that a nozzle communicating with the liquid conveying means is provided to produce a cohesive surface film between the container or reactor wall and the nozzle and in that the reactor has an inlet and an outlet to enable the gas to be passed through the surface film. This apparatus has the advantage that it is equally suitable for the treatment of polluted liquids and gases, the use of the nozzle having the great advantage that the radiation emission is not impaired. The nozzle may, for example, have an annular gap through which the liquid under pressure emerges. In this way a thin surface film can be produced which the gas must pass through on the way through the reactor. Advantageously the gas is introduced into the container. Advantageously the gas introduced into the container in countercurrent to the falling film. Advantageously, the nozzle has a rotationally symmetrical approximately pear-shaped inner space with an outwardly curved outlet, for example an outlet widened to be trumpet shaped, the supply line or inlet leading tangentially into the nozzle inner space. A cohesive compact surface film can be formed by means of a a spin nozzle of the kind known, for example, from EPA-0 204 709, the gas passing through said surface film practically as through a microfilter. In this way it is possible to ensure a practically complete contacting of the gas with the liquid. The advantage of this nozzle resides in the fact that the surface film produced is very stable so that the gas flow can be relatively high. Also, the amount of liquid for producing the surface film is relatively small. In addition, as a result of the rotation of the film pollution particles in the gas are conveyed outwards to the container wall and absorbed by the flowing film liquid. In contrast to a Raschig column, solids cannot lodge in the nozzle of EP-A-0 204 709 and clog it after some time. A long service life can thus be ensured.

Advantageously, the reactor is tubular and the nozzle is disposed concentrically in the tube. Ideally, the elongate (UV) radiator extends through the entire reactor so that the gas passed therethrough is continually exposed to the radiation. This means that no immersion well is used which absorbs a part of the radiation due to a second current lead required but a UV-reactor which is open at the top and at the bottom, thus enabling to apply the highest possible radiation density in the UV-reactor without incurring energy losses due to the absorption of the second lead wire and the pipe necessary to carry cooling medium (air or nitrogen) to the bottom part of the immersion well.

It is also advantageous for the radiation source to be disposed on the nozzle axis. This gives a compact reactor construction. Since, moreover, the radiation is present everywhere, i.e. there are no dead spaces, the reactor is also excellent for the sterilization of water since no bacteria nests can be formed in the reactor. However, it is quite feasible to dispose the radiation source outside the reactor and to use a reactor wall made from a radiation-transparent material. It is also possible to provide a plurality of nozzles one beneath the other in a reactor tube. The reactor efficiency can be further improved by forming a plurality of surface films. Advantageously, means are provided to collect the liquid and pass it successively through the individual nozzles. A further improvement can be achieved if the reactor inner wall has a radiation-reflecting coating. If the reactor is formed from a radiation-transparent material, e.g. quartz in the case of UV radiation, a second trickling film, e.g. for the additional supply of polluted liquid, on the reactor outer wall can be simultaneously irradiated. The purification process efficiency can thus also be increased. Alternatively, a housing or a jacket can be provided, which surrounds the reactor and thus forms an annular space for supplying the polluted liquid. The distance between the two containers determines the thickness of the layer of irradiated liquid. The layer thickness can be selected and regulated according to the composition and the concentration of the pollutants for removal and the intensity of the radiation source. Advantageously, the outer container consists of stainless steel with reflecting inner walls.

One advantageous embodiment comprises combining a plurality of tubes to form a tube or reactor bundle. The capacity of the resulting reactor can thus be substantially increased. Advantageously, a collecting basin is provided for the down-flowing liquid and communicates with the liquid conveying means. The liquid can as a result be used practically as often as desired. It may be advantageous to provide a connection between the gas inlet and the gas outlet so that the gas can be repeatedly fed through the reactor. Advantageously, a supply line is provided for supplying liquid and/or adding a compound, e.g. hydrogen peroxide, which is activatable by irradiation. Accelerated decomposition of the compounds, usually organic compounds, present can thus be achieved in the liquid.

The method according to the invention and the apparatus for performing the method are suitable not only for the purification and/or the sterilisation of drinking water, industrial waste water, etc., but also for deodorising gases or liquids.

BRIEF DESCRIPTION OF THE DRAWINGS

Exemplified embodiments of the invention are described below with reference to the drawings wherein:

Referring to FIG. 1, the reactor 11 consists essentially of a tube 13, in which a nozzle 15 and a radiation source 17 are disposed. The nozzle 15 has a pear-shaped inner space 19, which widens out at the bottom to form an outlet 21 in the form of a trumpet. The shape of the nozzle can also be compared with that of a bell. A line or inlet 23, through which liquid can be conveyed into the nozzle 15, leads tangentially into the inner space 19. If the liquid is pumped into the inner space 19 under pressure, it forms a cohesive rotating liquid layer 27 on the inner wall 25 of the nozzle 15. In these conditions, the liquid of the layer 27 travels through the neck of the nozzle 15 to the outwardly curved outlet 21, where it is deflected practically perpendicularly to the axis of rotation 19 by the action of centrifugal force. In these conditions, a continuous surface film 31 forms between the nozzle 15 and the tube 13, through which a gas for purification can be passed. Thus, the important factor is that a cohesive surface film 31 is so formed by a suitable nozzle— more particularly a spin nozzle as described in EP-A-0 204 709—that a flow of gas passed through a gas inlet 47 into the tube 13 must pass the surface film 31 and a transfer of gaseous pollutants into the liquid can take place. Since the radiation source 17 also extends beneath the nozzle. radiation absorbing pollutants can, in the actual gas phase, absorb the energy emitted by the radiation source 17 and at least be partially decomposed. The remaining pollutants are largely absorbed by the washing liquid on passing the surface film 31, and the purified flow of gas can leave the reactor 11 through the gas outlet 49. The liquid together with the pollutants leaving the surface film 31 then flows in the form of a falling or trickling film 33 down along the tube inner wall 35. In these conditions, the liquid is further exposed to the radiation so that an extensive decomposition of the pollutants can be effected. In order to increase the decomposition effects, the reactor inner wall 35 may additionally have a reflecting coating. By means of an outlet 34 at the bottom of the reactor the liquid can either be removed from the reactor or be pumped back to the nozzle 15 by means of a pump 69.

Figure 1:
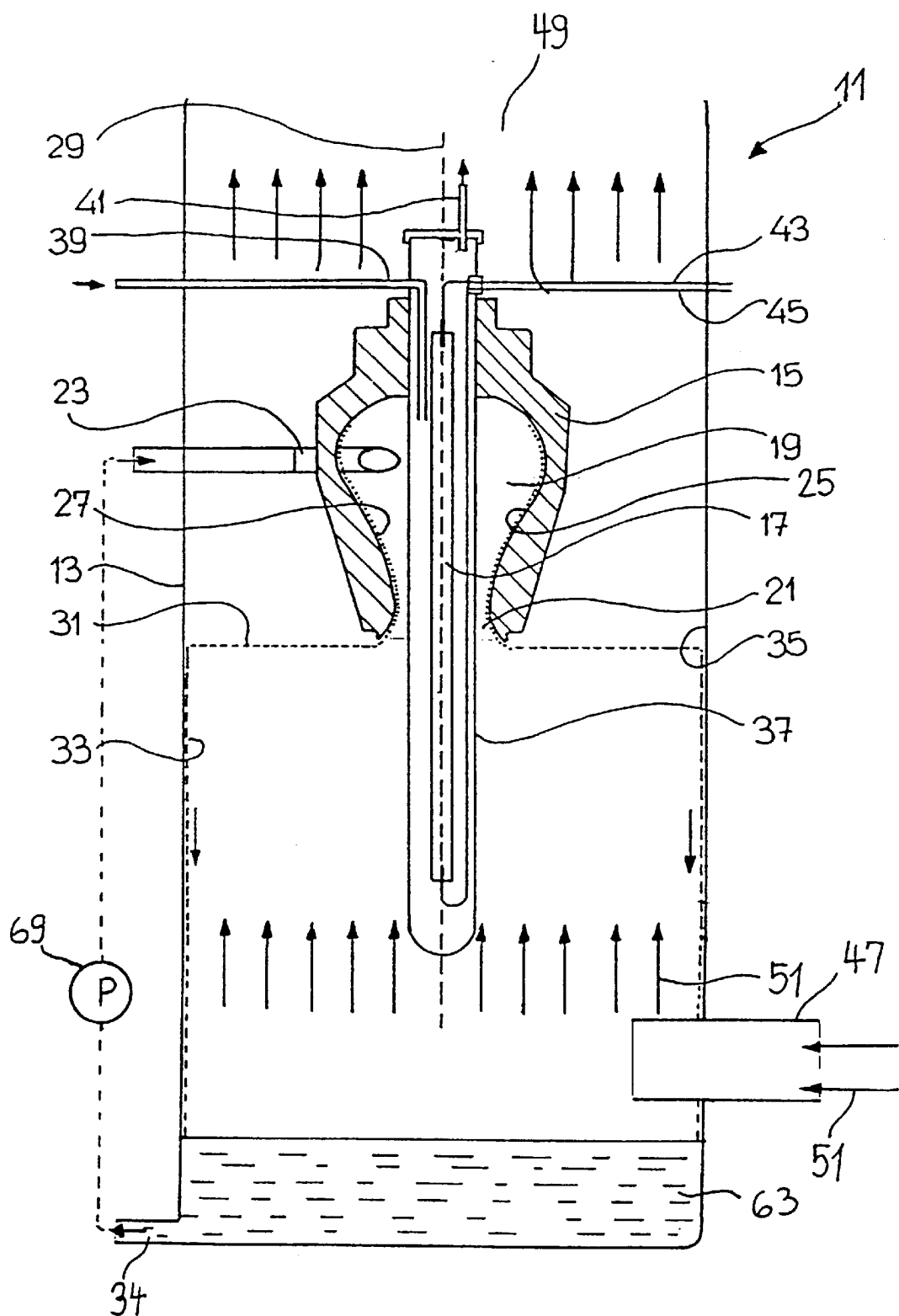
FIG. 1 is a schematic elevational view of a reactor formed from a cylindrical tube, with a nozzle and radiation source shown in longitudinal section.

The radiation source 17, e.g. a mercury high-pressure lamp or a metal halide lamp for generating selective emission bands, is preferably disposed concentrically to the nozzle 15 and extends through the latter. The advantage of this is that the liquid entering the inner space 19 can already be irradiated, for example in order to activate and oxidant, e.g. hydrogen peroxide, added to the liquid. The lamp 17 is accommodated in a closed radiation-transparent protective tube 37. An inlet and outlet spigot 39, 41 for a coolant lead into the protective tube 37. The electrical leads 43,45 for the lamp 17 are also taken through the protective tube 37. As will be seen from FIG. 1, the surface film 31 does not touch the protective tube 37. The advantage of this is that the transparency of the protective tube 37 to the electromagnetic radiation is not impaired by the decomposition reaction, even after long periods of operation.

A flow of gas 51 for purification (FIG. 1) is passed into the tube through the bottom gas inlet 47 and, after passing through the surface film 31, is taken out through the top gas outlet 49. The positive pressure of the gas is so adjusted that the surface film 31 is substantially maintained in operation.

Figure 2:
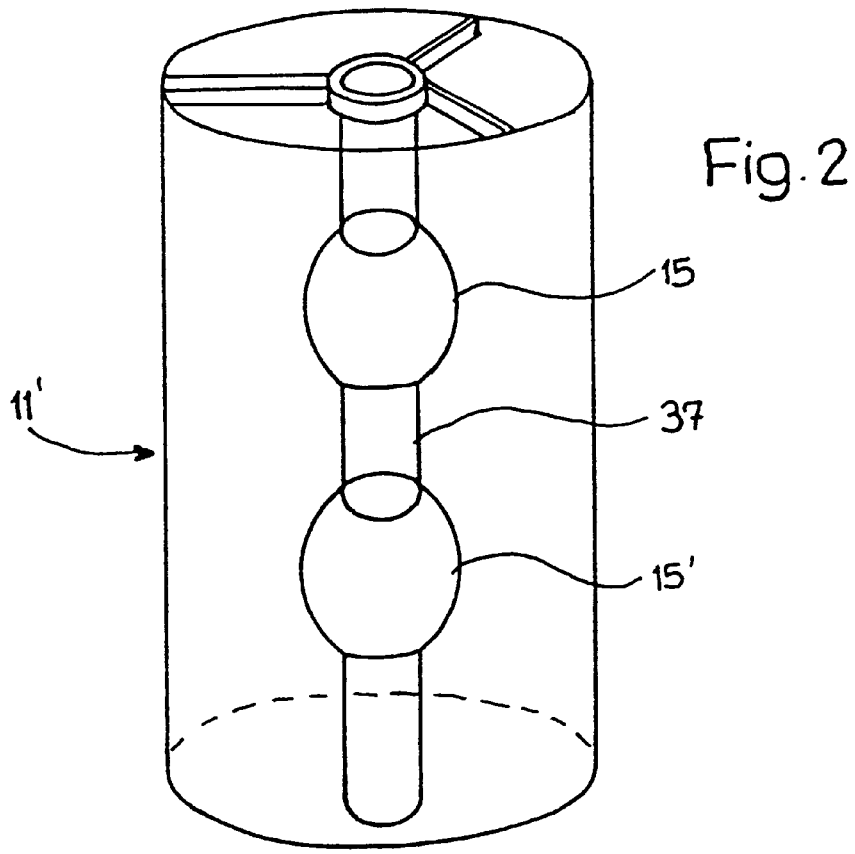
FIG. 2 is a perspective view which shows another exemplified embodiment with two nozzles.

FIG. 2 diagrammatically illustrates another reactor 11', which differs from the first reactor only in that two nozzles 15,15' are provided at the radiation source 17 or the protective tube 37 surrounding the same. Of course an even larger number of nozzles 15 may be provided. The nozzles disposed consecutively or in series have the advantage that the flow of gas for purification is repeatedly contacted with the liquid. One particular embodiment is obtained if the liquid flowing down from the upper nozzle 15 is collected in a trough disposed on the tube inner wall above the nozzle 15' therebeneath (not shown in the drawing) and is pumped by a pump via a line (not shown in the drawing) into the nozzle 15' therebeneath. The liquid can thus be purified in stages, almost cascade fashion, the purity of the liquid increasing from nozzle to nozzle.

Figure 4:
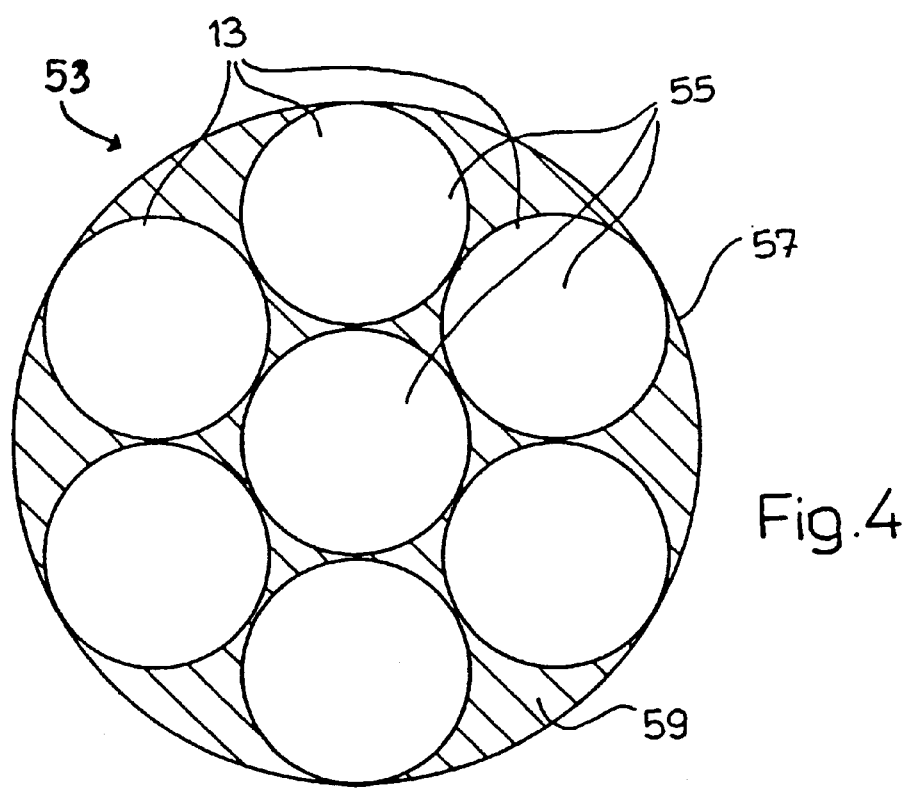
FIG. 4 is a plan view of the reactor shown in FIG. 3.
Figure 3:
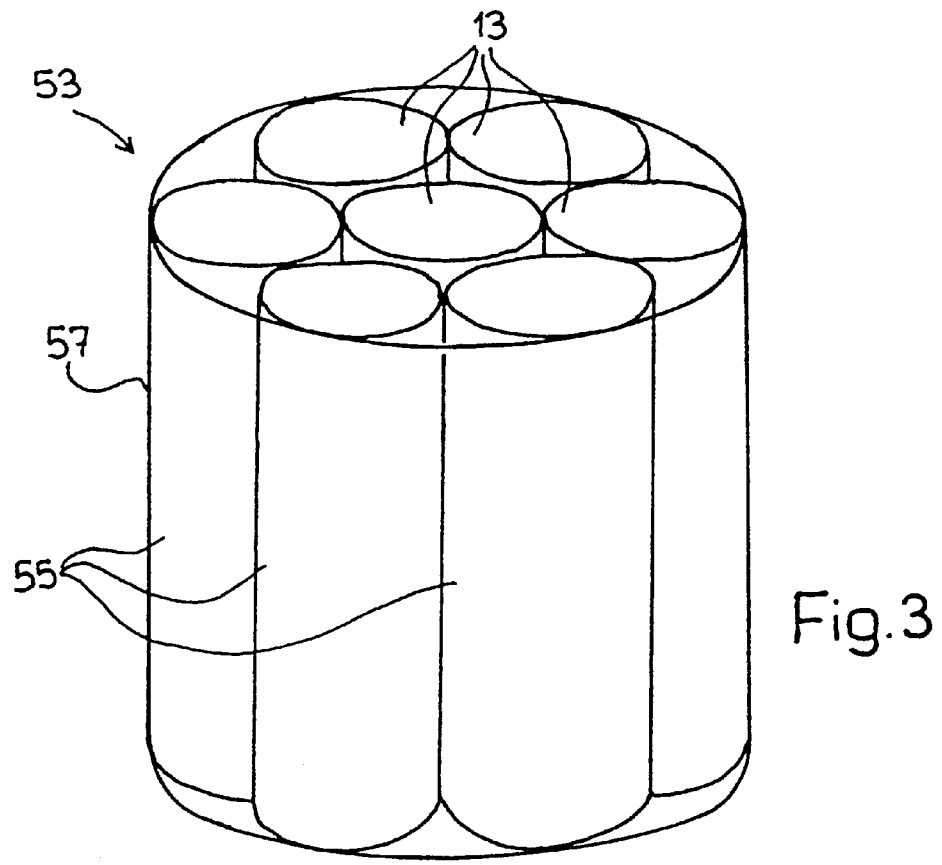
FIG. 3 is a perspective view of a reactor comprising a plurality of tubular reactors combined to form a nest.

FIGS. 3 and 4 show a reactor 53 comprising a plurality of reactor tubes. The tubes 13 are combined to form a reactor or tube nest 55, which is held together by a perforate metal plate 59. The tube nest 55 itself is disposed in a cylindrical jacket 57. This reactor 53 permits a high air throughput and therefore has a high purification capacity.

Figure 5:
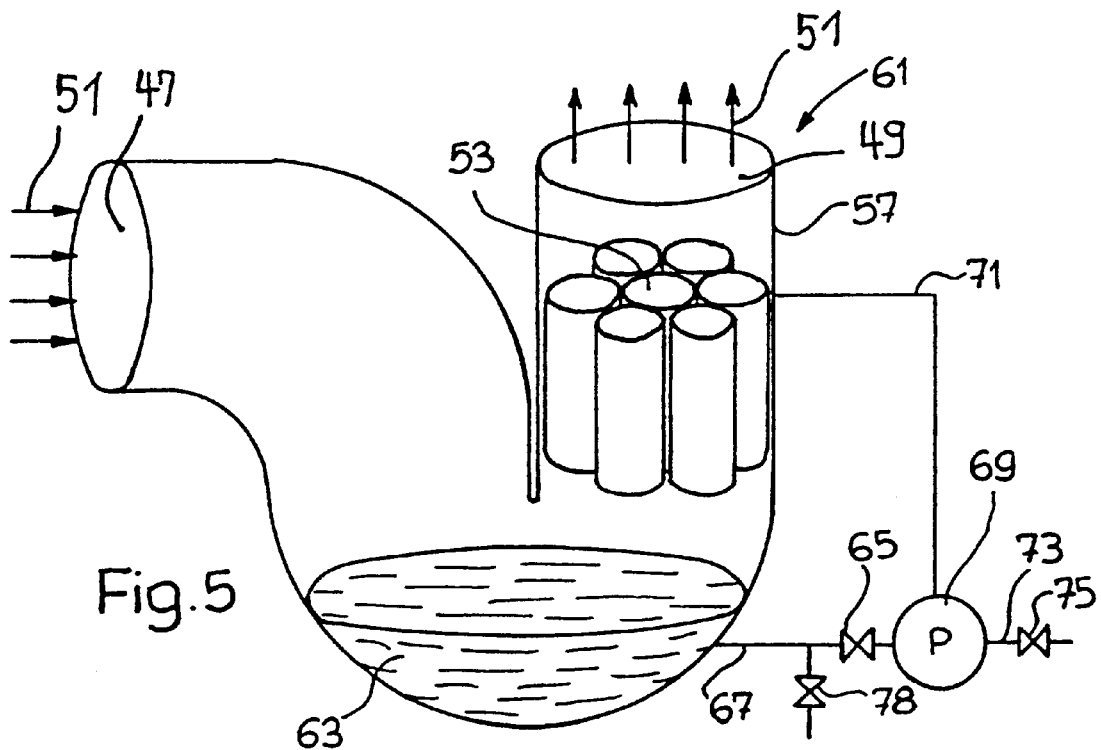
FIG. 5 is a sketch of a purification apparatus with the reactor of FIG. 3, and FIG. 6 diagrammatically shows an exemplified embodiment of a reactor with a double jacket.

FIG. 5 illustrates by way of example a purification device 61 comprising a reactor nest 55 and having a collecting basin 63. The latter is connected to a pump 69 via a line 67 comprising a valve 65. The pump 69 conveys the liquid flowing out of the reactor 53 to the nozzles 15 via the line 71, so that a continuous liquid circulation is obtained. Additional liquid can be fed via the supply line 73 containing a valve 75 or alternatively an oxidant can be added. The valve 78 serves to discharge the liquid.

Figure 6:
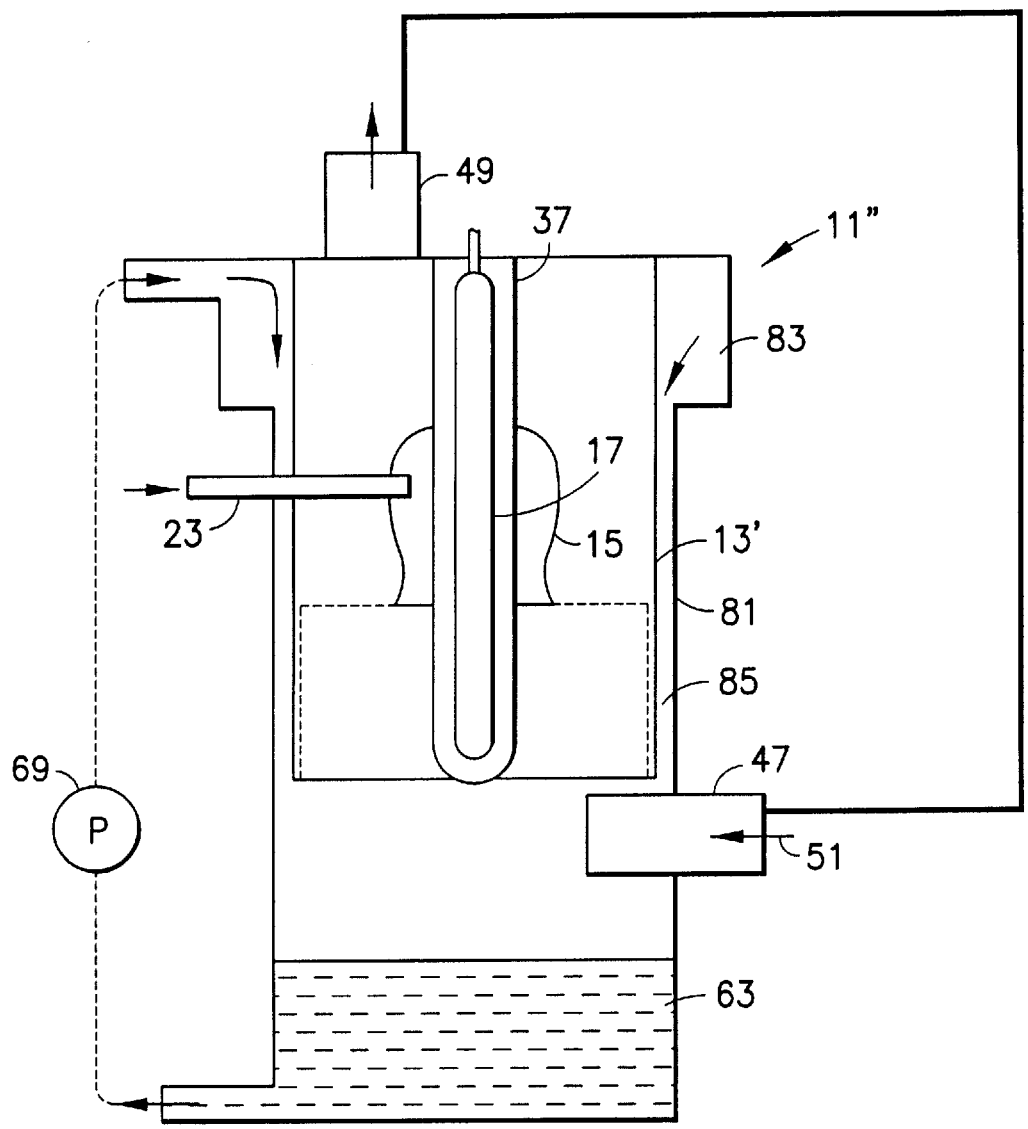

The reactor 11" shown diagrammatically in FIG. 6 is accommodated in a reactor housing 81. A gap or annular space 85, through which the liquid for treatment is partially taken, is provided between the reactor housing jacket and the tube 13'. The latter is made from a material from a material transparent to the radiation so that the liquid flowing through the annular space 85 is also irradiated during operation. To enable a uniform falling film to form in the annular space 85 the housing 81 is widened out at the top to form a reservoir 83.

The reactor is used as follows: a liquid, e.g. water, is conveyed by the pump 69 via the lines 67, 71 from the collecting basin 63 to the nozzles 15. The latter form a continuous liquid curtain in the reactor 53 (FIG. 5). The water flows in the form of a falling film along the tube inner walls into the collecting basin 63 therebeneath. At the same time, the radiation source 17, preferably a mercury high-pressure or low-pressure lamp, is switched on. The use of other radiation sources e.g. alpha, gamma-radiators for sterilising waste air or waste water is also feasible.

The gas flow for purification is preferably introduced into the reactor and through the surface film from the bottom, i.e. in countercurrent flow to the falling film. On the way through the reactor the gas flow 51 is irradiated by the radiation source 17 so that pollutants are already decomposed in the gas phase and/or micro-organisms can be rendered harmless. Any pollutants or decomposition products thereof from the gas phase are transferred, by the subsequent contact with the surface film 31, to the liquid phase in which they are decomposed by the simultaneous irradiation or by reaction with a suitable reagent, e.g. a strong oxidant, or a compound e.g. hydrogen peroxide, which can be activated by irradiation. The entire decomposition process is controlled by selective measurement to measure the radiation absorption. The measurement is preferably carried out at a plurality of points, namely at the inlet and outlet of the reactor and therebetween. The measurement signals are used in an automated process to control the liquid and gas transport and, possibly, the radiation intensity.

To summarise, it may be stated that the efficiency for the decomposition of pollutants which may occur in the gas or liquid phase is increased by a flowing surface film, more particularly a rotating surface film, which blocks the passage of a tubular reactor. As gas is passed through the reactor there is an effective contacting of the gas with the liquid so that a mass transfer can take place. The shape of the reactor and of the nozzle can basically depart from the embodiments described provided that the nozzle used generates a substantially cohesive stable surface film which divides the reactor inner space into two sections divided by the surface film and the gas has to pass the surface film or its edge zones on passage through the reactor.

We claim:

1. A method of treating gases or liquids or both gases and liquids containing pollutants in a reactor having an inner wall and a passageway adjacent thereto, the method comprising:
   (a) introducing a liquid into a nozzle disposed in the reactor to form a cohesive surface film in the passageway of the reactor, said liquid flowing down the reactor inner wall in the form of a falling film and is simultaneously exposed to an electromagnetic radiation, and
   (b) passing a gas through the cohesive surface film in the passageway in the reactor so that mass transfer takes place from the gas phase to the liquid phase.

2. The method according to claim 1, wherein the gas and the liquid are irradiated simultaneously with the electromagnetic radiation.

3. The method according to claim 1 wherein the gas is supplied countercurrent relative to the falling film.

4. The method according to claim 1, wherein a rotating surface film is produced in the reactor.

5. The method according to claim 1, wherein at least one reagent or compound activatable by irradiation and capable of reacting with at least some of the pollutants in the gas or liquid is added to the gas or the liquid or both the gas and the liquid.

6. The method according to claim 1, wherein the liquid is circulated.

7. The method according to claim 6, wherein the gas is partially circulated.

8. A method of treating gases or liquids or both gases and liquids containing pollutants in a reaction having an inner wall and a passageway adjacent thereto, the method comprising:

(a) introducing a liquid into a nozzle to form a cohesive surface film in the passageway of the reaction, said liquid flowing down the reactor inner wall in the form of a falling film and being simultaneously exposed to an electromagnetic radiation,
(b) passing a gas through the cohesive surface film in the passageway of the reactor so that mass transfer takes place from the gas phase to the liquid phase, and
(c) measuring the concentration of at least some of the pollutants and, on the basis of said measuring, controlling at least one of the following:
   (i) the supply and discharge of the gas or the liquid or both the gas and the liquid containing pollutants,
   (ii) the number of passes through the reactor of the liquid or of the gas or both the liquid and the gas, and
   (iii) the intensity of the radiation.

9. The method according to claim 8, further comprises measuring the absorption of the liquid or of the gas or of both the liquid and the gas selectively at more than one point.

10. The method according to claim 9, wherein the adsorption is measured at the inlet, the outlet and at a position therebetween.

11. The method according to claim 8, wherein process parameters selected from the group consisting of the pH, the redox potential, the conductivity and the temperature, are measured and used to control the purification process.

12. The method according to claim 8, wherein the supply and discharge of the gas or the liquid or both the gas and the liquid are controlled.

13. The method according to claim 8, wherein the number of passes through the reactor of the liquid and of the gas or both the liquid and the gas is controlled.

14. The method according to claim 8, wherein the intensity of the radiation is controlled.

15. An apparatus for the treatment of gases or liquids or both gases and liquids containing pollutants, comprising a reactor having an inner wall and a passageway adjacent thereto, at least one radiation source disposed in the reactor for irradiation of the reactor interior with electromagnetic radiation, a top inlet in the reactor for introducing the liquid and a bottom outlet in the reactor for removing the liquid, a conveyor to convey the liquid to the liquid inlet, at least one nozzle communicating with the conveyor and disposed in the reactor to generate a cohesive surface film between the inner wall of the reactor and the nozzle, a gas inlet in the reactor and a gas outlet in the reactor to enable a gas to be passed through the cohesive surface film.

16. The apparatus according to claim 15, wherein the nozzle has a rotationally symmetrical inner space with an outwardly curved outlet and the top inlet for the liquid leads tangentially into the inner space of the nozzle.

17. The apparatus according to claim 16, wherein the inner space of the nozzle is pear-shaped.

18. The apparatus according to claim 15, wherein the reactor is formed from a vertically disposed tube and the nozzle is disposed concentrically in the tube.

19. The apparatus according to claim 18, which further comprises a housing which surrounds the tube to form an annular space between the tube and the housing, for supplying the liquid.

20. The apparatus according to claim 15, wherein a plurality of tubes are combined to form a reactor bundle.

21. The apparatus according to claim 15, further comprising a collecting basin for the liquid flowing from the reactor, said collecting basin communicating with the conveyor.

22. The apparatus according to claim 15, wherein a connection is provided between the gas inlet and the gas outlet to circulate the gas.

23. The apparatus according to claim 15, which further comprises a supply line for supplying liquid or for adding a compound activatable by irradiation.

24. The apparatus according to claim 15, radiation source is disposed on a substantially central longitudinal axis of the nozzle.

25. The apparatus according to claim 15, wherein a plurality of said nozzles are disposed beneath one another.

26. The apparatus according to claim 25, wherein a collector is provided to collect the liquid and pass the liquid successively through the plurality of individual nozzles.

27. The apparatus according to claim 15, wherein the inner wall of the reactor is made of a radiation-transparent material.

28. The apparatus according to claim 15, wherein the inner wall of the reactor has a radiation-reflecting coating.

* * * * *